United States Patent
Yokoi et al.

(10) Patent No.: US 7,448,993 B2
(45) Date of Patent: Nov. 11, 2008

(54) GASTROINTESTINAL TRACT EXAMINING APPARATUS

(75) Inventors: Takeshi Yokoi, Hino (JP); Hironobu Takizawa, Hachioji (JP); Hidetake Segawa, Hachioji (JP); Akira Kikuchi, Yokohama (JP)

(73) Assignee: Olympus Corporation, Tokyo (JP)

( * ) Notice: Subject to any disclaimer, the term of this patent is extended or adjusted under 35 U.S.C. 154(b) by 67 days.

(21) Appl. No.: 10/951,100

(22) Filed: Sep. 27, 2004

(65) Prior Publication Data
US 2005/0085697 A1 Apr. 21, 2005

(30) Foreign Application Priority Data
Sep. 30, 2003 (JP) .............................. 2003-342417

(51) Int. Cl.
*A61B 1/00* (2006.01)

(52) U.S. Cl. .................. 600/114; 600/101; 600/109; 600/117; 600/127; 600/129; 600/160; 600/173

(58) Field of Classification Search .................. 600/114
See application file for complete search history.

(56) References Cited

U.S. PATENT DOCUMENTS

| | | | | |
|---|---|---|---|---|
| 4,198,960 A | * | 4/1980 | Utsugi | 600/104 |
| 5,653,677 A | * | 8/1997 | Okada et al. | 600/112 |
| 5,741,429 A | * | 4/1998 | Donadio et al. | 216/8 |
| 6,632,171 B2 | * | 10/2003 | Iddan et al. | 600/106 |
| 6,689,056 B1 | * | 2/2004 | Kilcoyne et al. | 600/300 |
| 6,884,213 B2 | * | 4/2005 | Raz et al. | 600/104 |
| 6,986,738 B2 | * | 1/2006 | Glukhovsky et al. | 600/109 |
| 2004/0133076 A1 | * | 7/2004 | Kobayashi et al. | 600/175 |

FOREIGN PATENT DOCUMENTS

| | | |
|---|---|---|
| JP | 6-142081 | 5/1994 |
| JP | 2002-000556 | 1/2002 |
| JP | 2003-135388 | 5/2003 |
| JP | 2003-210393 | 7/2003 |
| JP | 2004-49754 | 2/2004 |
| JP | 2004-49756 | 2/2004 |
| WO | WO 99/32028 | 7/1999 |
| WO | WO 01/89596 A2 | 11/2001 |

* cited by examiner

*Primary Examiner*—Linda C. M. Dvorak
*Assistant Examiner*—Matthew J Kasztejna
(74) *Attorney, Agent, or Firm*—Scully, Scott, Murphy & Presser, P.C.

(57) ABSTRACT

A gastrointestinal tract examining apparatus includes a capsular endoscope which examines the gastrointestinal tract, a flexible tube member, a flexible string member which is inserted in the tube member, and a connecting portion which is arranged to the capsular endoscope. In the gastrointestinal tract examining apparatus, the tube member is separated from the capsular endoscope by detachably connecting the string member to the connecting portion.

28 Claims, 12 Drawing Sheets

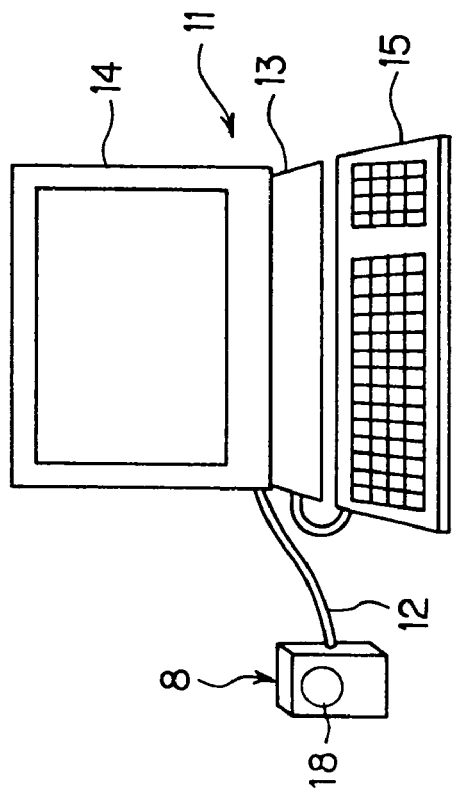
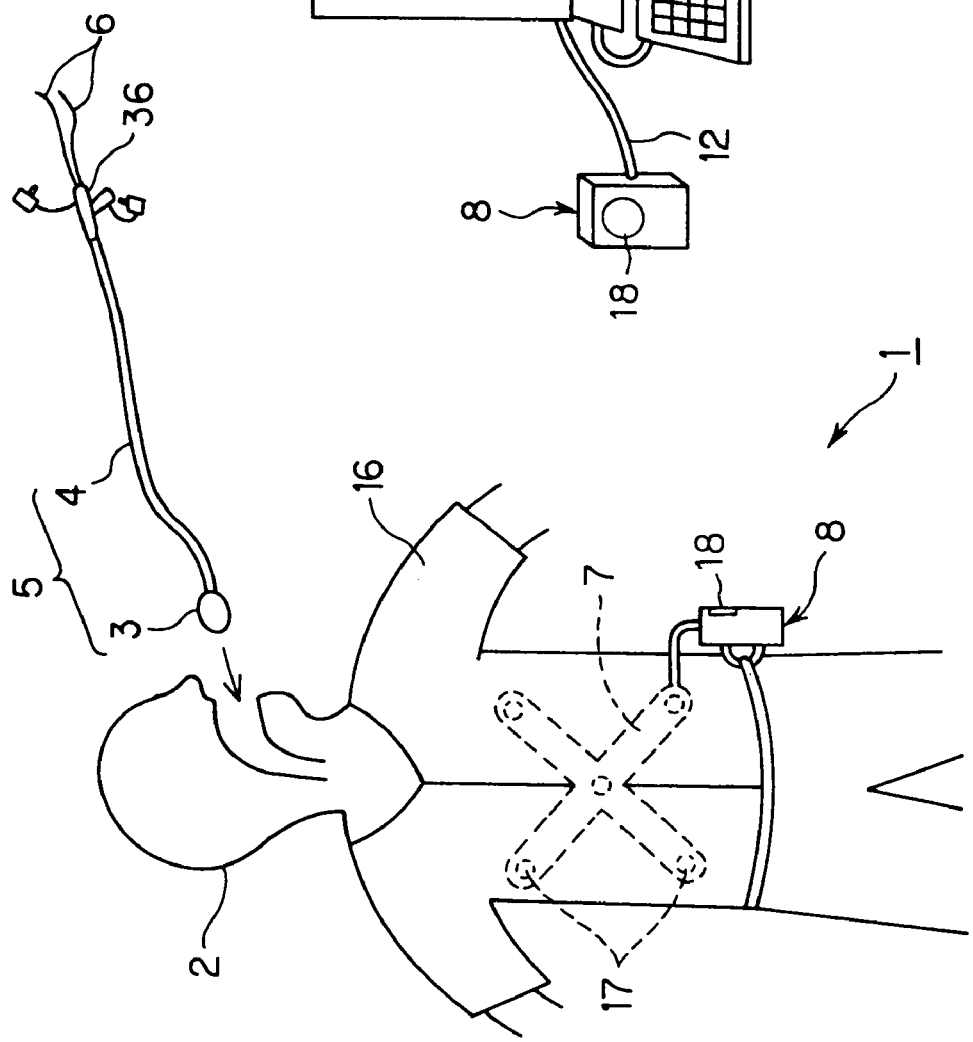

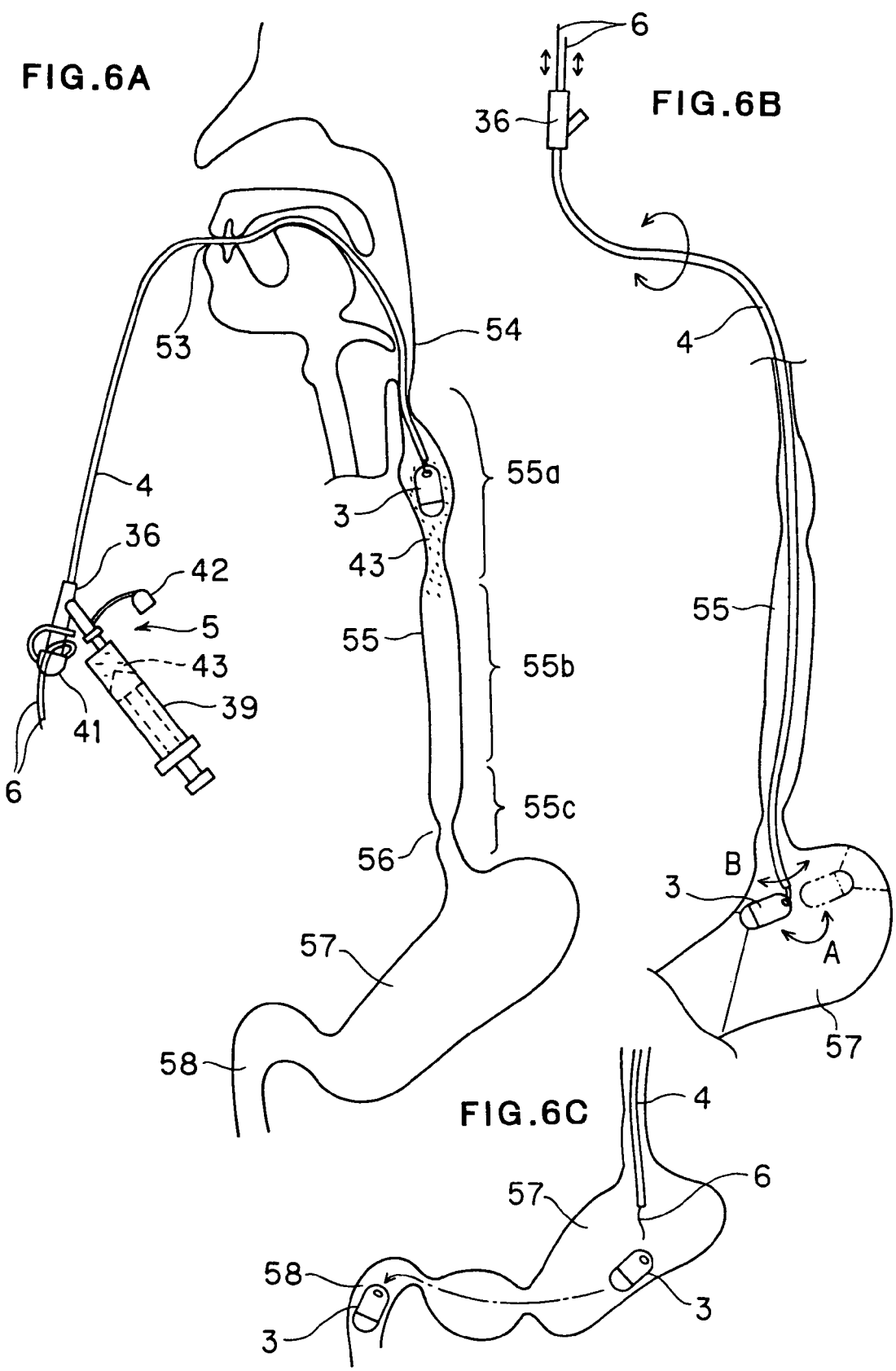

GASTROINTESTINAL TRACT EXAMINING APPARATUS

This application claims benefit of Japanese Application No. 2003-342417 filed on Sep. 30, 2003, the contents of which are incorporated by this reference.

BACKGROUND OF THE INVENTION

1. Field of the Invention

The present invention relates to a gastrointestinal tract examining apparatus which is suitable to the examination of the gastrointestinal tract.

2. Description of the Related Art

Various capsular medical apparatuses are suggested for the examination of the body cavity. For example, as a first conventional art, PCT international publication No. WO99/32028 discloses one capsular medical apparatus, in which a capsule is held by clamp means, in this state, an endoscope with a flexible line is inserted in the body cavity together with the capsule, and the holding state of the capsule is reset at a target position.

According to the first conventional art, the clamp means holds the outer body of the capsule, and the outer diameter in the holding state is larger than the outer diameter of only the capsule.

Further, as a second conventional art, PCT international publication No. WO01/89596A2 discloses another capsular medical apparatus, in which a capsule is sucked and is held at the remote end of a tube having the remote and near ends, which is filled with a solution, and the capsule is released by discharging the suction at the target position.

Furthermore, as a third conventional art, Japanese Unexamined Patent Application Publication No. 2003-135388 discloses another capsular medical apparatus, in which a tube member with a needle with the structure of double tube is attached to a rubber stopper at the rear end of a capsule with a balloon, and a needle-shaped thin diameter portion is accommodated in an outer cylinder with double tube upon resetting the connection to the capsule.

SUMMARY OF THE INVENTION

According to the present invention, a gastrointestinal tract examining apparatus comprises:

a capsular endoscope which examines the gastrointestinal tract;

a flexible tube member;

a flexible string member which is inserted in the flexible tube member; and a connecting portion which is arranged to the capsular endoscope, wherein the tube member is separated from the capsular endoscope by detachably connecting the string member to the connecting portion.

BRIEF DESCRIPTION OF THE DRAWINGS

FIGS. 1A to 7 relate to a first embodiment of the present invention, FIG. 1A is a diagram showing the entire structure of a capsular endoscope system according to the first embodiment of the present invention;

FIG. 1B is a diagram showing an extracorporeal unit and a personal computer;

FIG. 2 is a diagram showing the entire basic structure of a capsular gastrointestinal tract examining apparatus;

FIG. 3 is a diagram showing the detailed structure of the capsular gastrointestinal tract examining apparatus;

FIGS. 6A to 6C are diagrams showing a using example and an examining method in the body;

FIG. 7 is a flowchart showing the sequence for a typical examining method;

FIG. 8A is a diagram showing the structure of a gastrointestinal tract examining apparatus having a temporary stop portion according to the second embodiment of the present invention;

FIG. 8B is a diagram showing a state in which the temporary stop is reset;

FIG. 9A is a diagram showing the structure of a main portion of a gastrointestinal tract examining apparatus according to third embodiment of the present invention;

FIG. 9B is a cross-sectional view of a line C-C in FIG. 9A;

FIG. 9C is a diagram showing a cotton thread which is cut off in a state shown in FIG. 9A;

FIG. 9D is a diagram showing the structure of a main portion of a gastrointestinal tract examining apparatus according to a modification of the third embodiment;

FIG. 10A is a diagram showing the structure of a main portion of a gastrointestinal tract examining apparatus according to the fourth embodiment of the present invention;

FIG. 10B is a diagram showing a state in which a thin portion is broken in FIG. 10A;

FIGS. 13A to 14 relate to a fifth embodiment of the present invention, FIG. 13A is a diagram showing the structure of a main portion of a gastrointestinal tract examining apparatus according to the fifth embodiment of the present invention;

FIG. 14 is a diagram showing the structure of a main portion of a gastrointestinal tract examining apparatus according to a modification of the fifth embodiment;

FIG. 17A is a diagram showing the structure of a main portion of a gastrointestinal tract examining apparatus according to the eighth embodiment of the present invention; and FIG. 17B is a diagram showing a state in which a capsule is set to be long in the horizontal direction.

DESCRIPTION OF THE PREFERRED EMBODIMENTS

Figure 2:
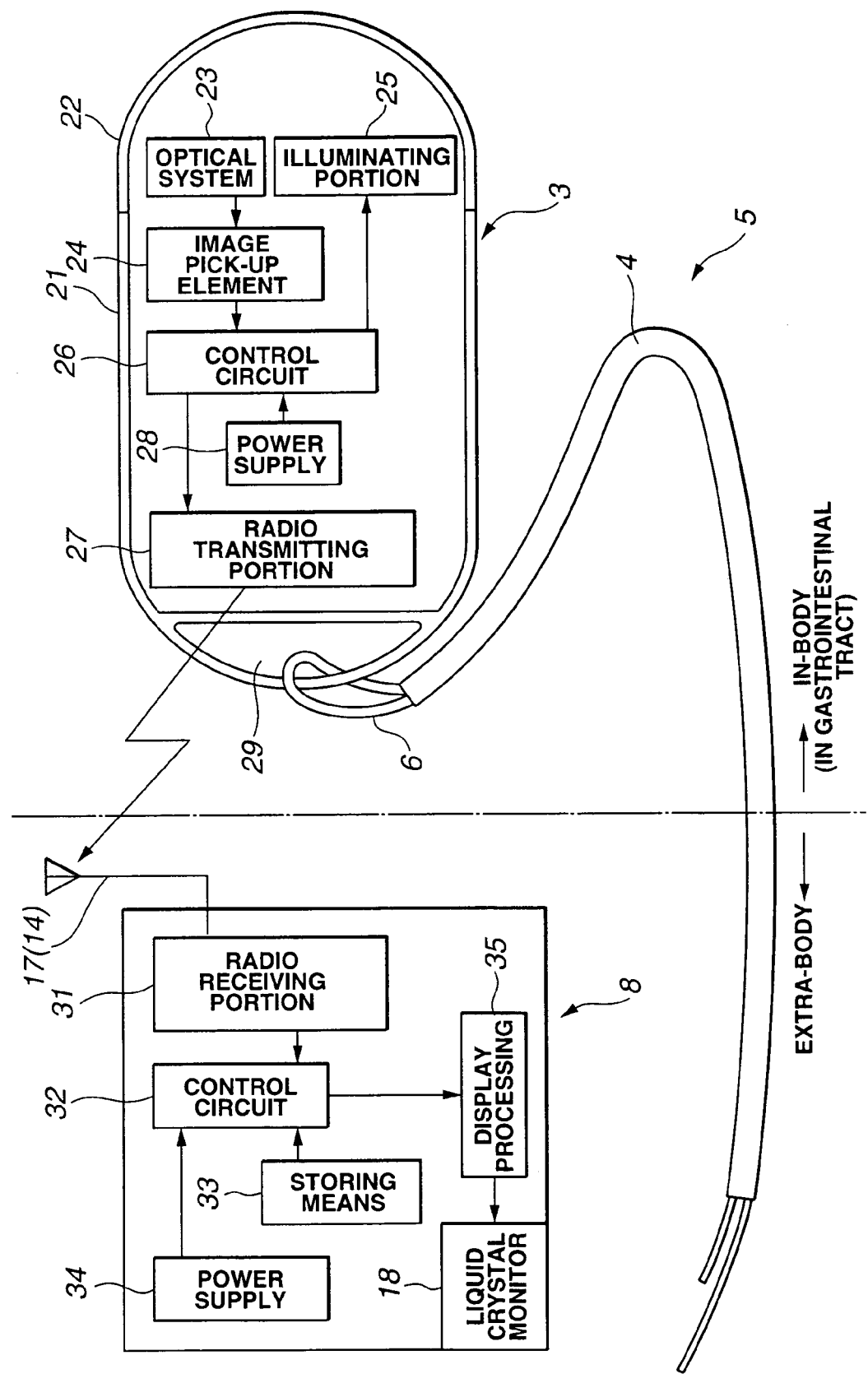

Hereinbelow, embodiments of the present invention will be described with reference to the drawings.

First Embodiment

A first embodiment of the present invention will be described with reference to FIGS. 1A to 7.

It is an object of the first embodiment of the present invention to provide a capsular gastrointestinal tract examining apparatus and an examining method which are capable of improving the inserting property and pull-out property in/from an examinee, of performing, with a simple method, both the returning examination in the esophagus and the untethered examination from the stomach on the deep side, and of examining, with a dye, the esophagus at the desired position.

Referring to FIG. 1A, a capsular endoscope system 1 according to the first embodiment comprises a gastrointestinal tract examining apparatus 5 comprising: a capsular endoscope (hereinafter, abbreviated to a capsule) 3 which is swallowed from the mouth of a patient 2 as an examinee, thus, passes through the line in the body cavity, specifically, gastrointestinal tract, and then transmits by radio an image signal that is obtained by optically picking-up an image of the inner surface of the gastrointestinal tract; and a tube member 4 which is detachably connected to the capsule 3 via a string member 6.

Further, the capsular endoscope system 1 comprises an extracorporeal unit 8 (extracorporeally arranged to the patient 2) having a function for receiving a signal transmitted by the capsule 3 via an antenna unit 7 arranged outside of the patient 2, and for storing an image.

Referring to FIG. 1B, the extracorporeal unit 8 is detachably connected to a personal computer (hereinafter, abbreviated to a PC) 11 by a cable such as a USB cable 12. Connected to the PC 11 are a PC main body 13 including a CPU and a hard disk which records an image, a display 14, as display means, which is connected to the PC main body 13 and which displays an image, and a key board 15 which inputs data. The image stored in the extracorporeal unit 8 is stored in the hard disk in the PC main body 13, and the stored image is displayed on a display 14.

Referring to FIG. 1A, when the capsule 3 is swallowed and an endoscope examination is performed as a medical action, the antenna unit 7 having a plurality of antennas 17 is attached to a shirt 16 worn by the patient 2. The antenna unit 7 receives the signal which is picked-up by the capsule 3 and then is transmitted from the antenna therein. The extracorporeal unit 8 connected to the antenna unit 7 stores the picked-up image.

The extracorporeal unit 8 comprises a liquid crystal monitor 18 which displays the image transmitted from the capsule 3. The extracorporeal unit 8 is attached to a belt of the patient 2 by a detachable hook.

FIG. 2 shows the basic structure of the extracorporeal unit 8 and the gastrointestinal tract examining apparatus 5.

Referring to FIG. 2, the capsule 3 comprises: an exterior member main body 21 which is cylindrical-shaped and has one end portion that is semi-spherical-shaped and is closed; and a semi-spherical transparent cover 22 which is fit and is fixed to another end portion as an opening of the exterior member main body 21. Thus, an exterior container is formed to the capsule 3 with the watertight structure.

The transparent cover 22 in the exterior container comprises an (objective) optical system 23 which forms an optical image of an observing object. At the image forming position, an image pick-up element 24 is arranged for picking-up an image such as a CMOS imager.

An illuminating portion 25 such as a white LED is arranged adjacently to the optical system 23 in the transparent cover 22 and it illuminates an image pick-up range (observing range) of the image formed on the image pick-up element 24 by the optical system 23.

The image pick-up element 24 comprises, on the rear surface side, a control circuit 26 which drives the illuminating portion 25, and drives the image pick-up element 24 and performs the signal processing and controls the image pick-up element 24, a radio transmitting portion 27 which transmits an image signal picked-up by the image pick-up element 24 to the extracorporeal unit 8, a power supply 28 such as a battery, which supplies power for opening the circuits, and the like. The radio transmitting portion 27 is connected to an antenna (not shown).

A through-hole 29 having a function of a connecting portion to the tube member 4 is arranged to the rear end of the exterior member main body 21 on the opposite side of the transparent cover 22. The string member 6 passes through the through-hole 29, thereby detachably connecting the capsule 3 to the tube member 4 via the string member 6.

That is, a folded portion of the string member 6 passes through the through-hole 29 and the two folded string members 6 are inserted in a hollow portion of the tube member 4, thereby inserting the capsule 3 connected to the tube member 4 in the body, specifically, the gastrointestinal tract.

The illuminating portion 25 arranged to the capsule 3 illuminates the target, the image of the illuminated inner wall or the like is picked-up by the optical system 23 and the image pick-up element 24, the endoscope examination is performed, the picked-up image information is extracorporeally transmitted to the body by radio, and the extracorporeal unit 8 which is arranged to the body outside receives the image information on the endoscope examination obtained by the capsule 3 via the antenna unit 7 and stores the image.

The extracorporeal unit 8 comprises: a radio receiving portion 31 which is connected to (the antennas 17 of) the antenna unit 7; a control circuit 32 which A/D-converts or compresses the signal received and demodulated by the radio receiving portion 31; storing means 33 which stores the image signal which is compressed via the control circuit 32; and a power supply 34 which supplies power to the control circuit 32 and another circuits.

A display processing circuit 35 is connected to the control circuit 32, thereby processing displaying the image transmitted from the capsule 3 on a liquid crystal monitor 18. Then, the user monitors the image picked-up by the image pick-up element 24 in the capsule 3, which is displayed on the liquid crystal monitor 18.

Figure 3:
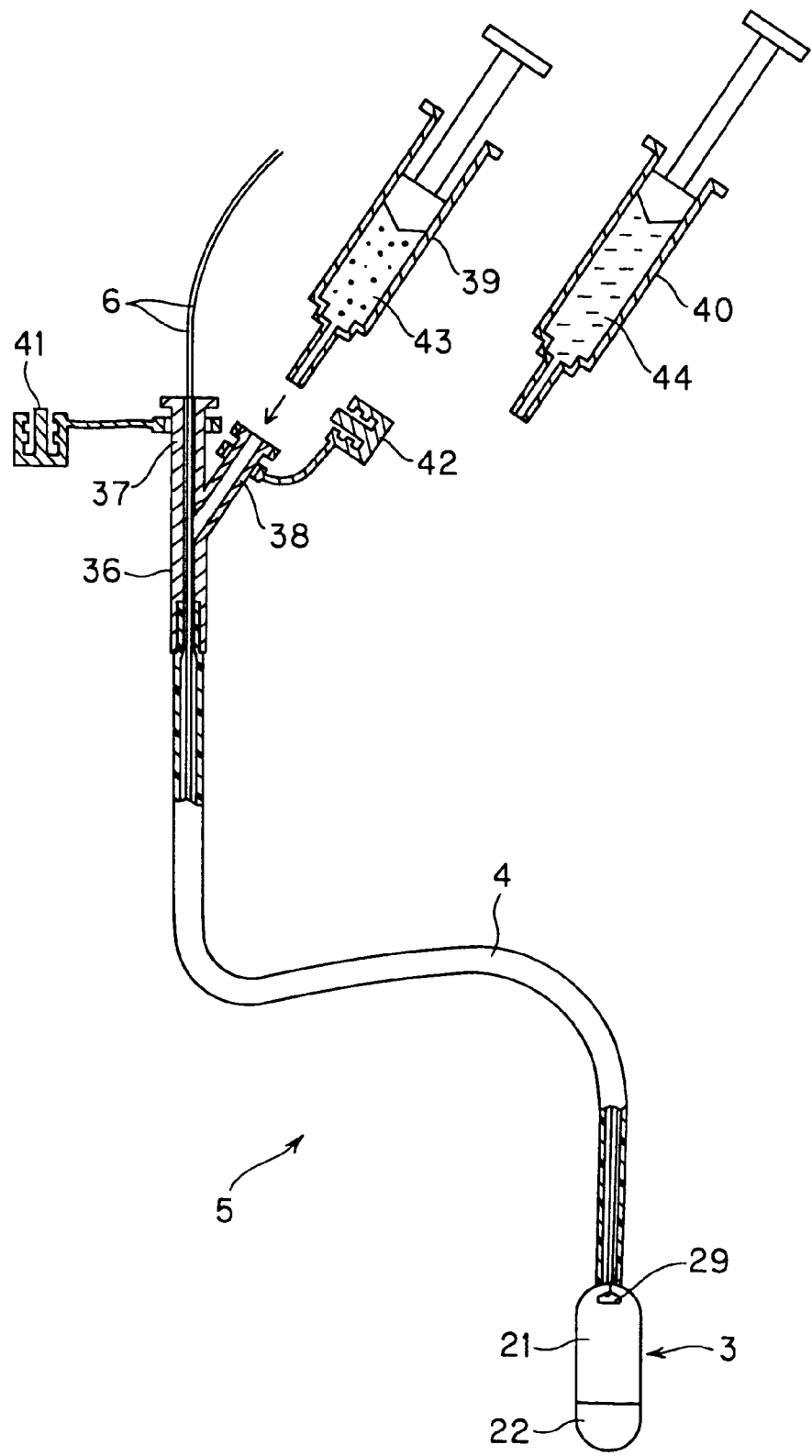

FIG. 3 shows the entire detailed structure of the gastrointestinal tract examining apparatus 5.

Referring to FIG. 3, the flexible tube member 4 has a folded portion through the through-hole 29 of the capsule 3 near the distal-end opening. The string member 6 folded by the folded portion is inserted in the hollow portion of the tube member 4, thereby connecting the capsule 3 to the tube member 4.

The rear end of the tube member 4 is connected to a tube member hand portion 36 which is substantially V-shaped and is branched by the adhesion or the like.

The tube member hand portion 36 comprises an extended hollow portion 37 which is extended to be directly connected to the hollow portion of the tube member 4 and a branched hollow portion 38 as a hollow portion that is diagonally branched in the halfway.

The extended hollow portion 37 is used for the insertion of the string member 6, and the branched hollow portion 38 has a function of a syringe inserting port in which the distal ends of syringes 39 and 40 are detachably inserted.

Near the rear end of the extended hollow portion 37, a stopper member 41 is integrally arranged to the tube member hand portion 36. The stopper member 41 is string member holding means which holds the inserting state of the string member 6 that is inserted by closing the opening of the extended hollow portion 37.

Further, near the rear end of the branched hollow portion 38, a stopper member 42 for closing the opening of the branched hollow portion 38 is integrally arranged to the tube member hand portion 36. In the case of using neither of syringes 39 and 40, the stopper member 42 closes the branched hollow portion 38.

The syringe 39 contains the dye for staining and observing (examining), e.g., an iodine solution 43 of 1.5% for iodine staining. By using the syringe 39, the staining and observation are possible.

The syringe 40 contains a transparent solution 44 such as cleaning water. By using the syringe 40, the dye for staining is washed or the mucus or bubbles are washed and cleaned.

Figure 4A:
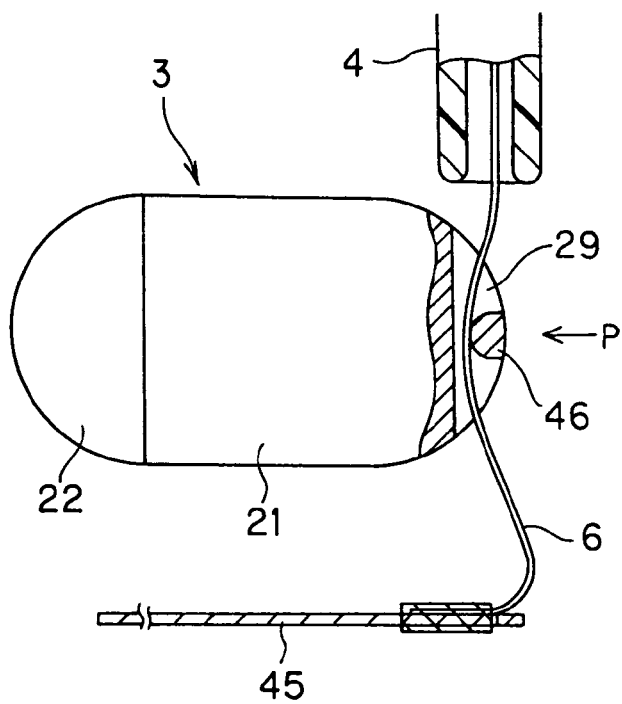
FIG. 4A is a diagram showing a cut-off part of the structure of a distal end portion of the gastrointestinal tract examining apparatus.
Figure 4B:
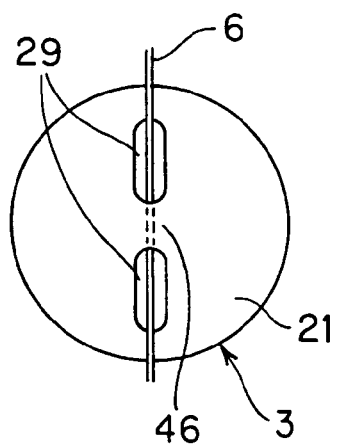
FIG. 4B is a diagram showing by an arrow P in FIG. 4A.
Figure 4C:
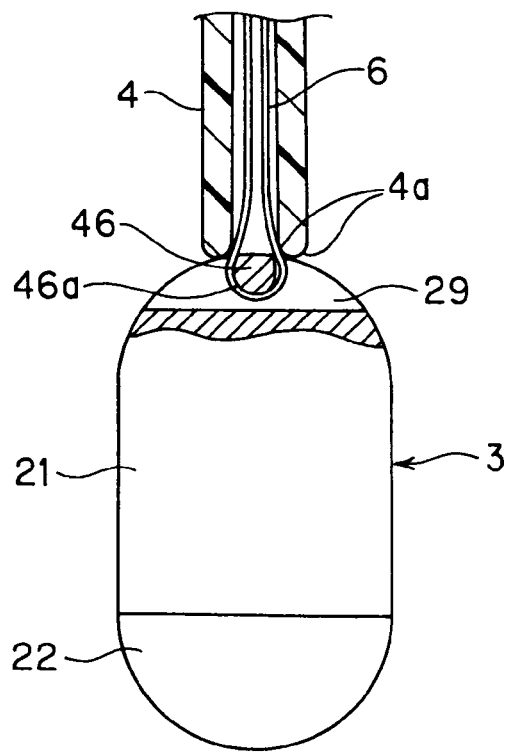
FIG. 4C is a diagram showing the connection between a tube member and a capsule.

Referring to FIG. 3, the connection to the capsule 3 is shown by using the string member 6 inserted in the tube member 4. Referring to FIGS. 4A to 4C, the sequence for connection to the capsule 3 is shown.

Referring to FIG. 4A, an inserting tool 45 such as a wire is previously fixed to the distal end of the string member 6 by taping, and is inserted in the hollow portion of the tube member 4, thereby inserting the string member 6 in the hollow portion of the tube member 4. The inserting tool 45 inserted in the hollow portion of the tube member 4 passes through the through-hole 29 in the capsule 3.

The through-hole 29 in this case has a locking portion 46 for locking the string member 6 in the center as shown in FIG. 4B indicated by an arrow P in FIG. 4A. Both sides of the locking portion 46 are elliptically notched.

As shown in FIGS. 4A and 4B, after the insertion in the through-hole 29, the inserting tool 45 passes through the hollow portion of the tube member from the distal end thereof again. Thus, referring to FIG. 4C, the tube member 4 is connected to the capsule 3 by using the string member 6 (inserted in the tube member 4).

In this case, as shown in FIG. 4C, a chamfered portion 4a is an R-chamfer, and is formed to the inner surface and the outer surface of a portion forming the distal-end opening of the tube member 4. The locking portion 46 between the through-holes 29 on the capsule 3 side has an R-shaped portion 46a along the through-holes 29. Thus, in a state that the string member 6 is inserted in the R-shaped portion 46a, even when the string member 6 is in contact with the wall surface of the locking portion 46, the string member 6 moves smoothly.

FIGS. 5A to 5D show examples of the structure of the tube member 4. The tube member 4 according to the first embodiment is flexible and is not compressive. When the tractive force acts to the string member 6 by an inserted string or the like, preferably, the tube member 4 has the property that the bending operation is difficult. Further, when the tube member 4 is pushed and pulled, preferably, it has the property that the bending operation is difficult.

Preferably, the tube member 4 is not more than the half of the outer diameter of the capsule 3, namely, 5 mm (more preferably, 2 to 3 mm) because the tube member 4 is easily inserted into the body cavity and the patient 2 easily swallows the capsule 3 upon insertion. Further, the tube member. 4 is excessively smaller than the outer diameter of the capsule 3, e.g., 10 mm. As mentioned above, the outer diameter of the tube member 4 is sufficiently thinner than the outer diameter of the capsule 3, and the tube member 4 is set to be flexible so that it is not easily bent when it is towed while the string member 6 is inserted in the hollow portion.

A description is given of examples of the specific structure of the tube member 4 with reference to FIGS. 5A to 5D.

Figure 5A:
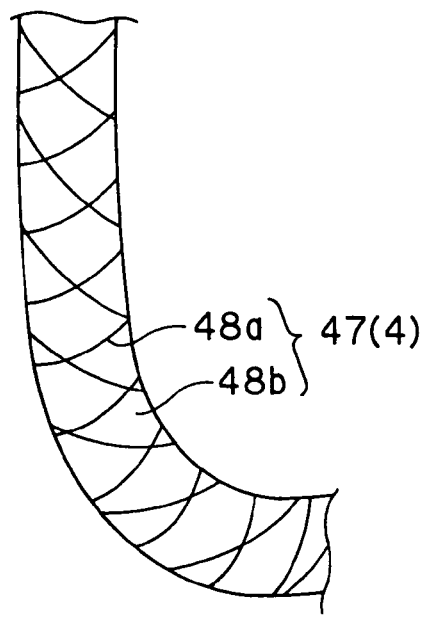
FIGS. 5A to 5D are diagrams showing examples of the structure of the tube member.

Referring to FIG. 5A, the tube member 4 comprises a torque tube 47. In the torque tube 47, a blade 48a is embedded in a flexible tube 48b.

Figure 5B:
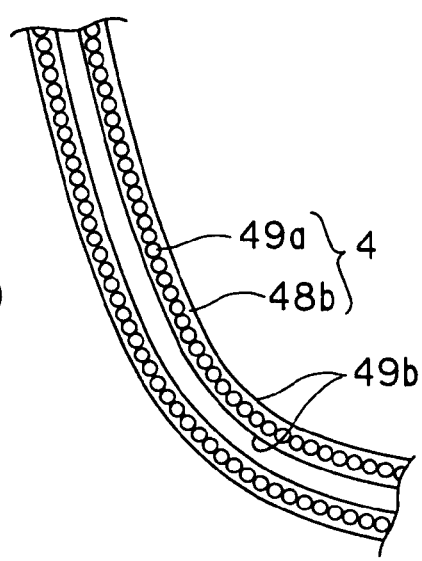

Referring to FIG. 5B, the tube member 4 is formed embedding a coil member 49a in the tube 48b. In this case, a coating film 49b for improving the smoothness may be formed on the outer and the inner surfaces. The coating film 49b containing fluorinated-system resin such as Teflon® has the preferable smoothness.

Figure 5C:
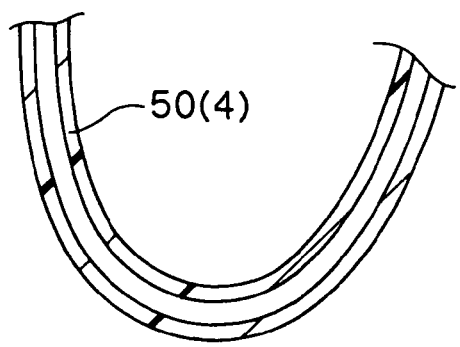

Referring to FIG. 5C, the tube member 4 is formed by a tube 50 containing fluorinated-system resin with the flexibility and the preferable smoothness such as PTFE (polytetrafluoroethylene) or PFA (perfluoroalkox resin). In this case, the tube member 4 is relatively thin.

Figure 5D:
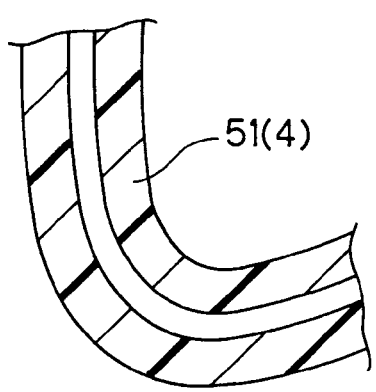

Referring to FIG. 5D, the tube member 4 comprises a thick resin tube 51 (poalon tube or the like) containing a material that is relatively soft and with the preferable smoothness such as polyvinyl chloride or urethane.

Figure 5E:
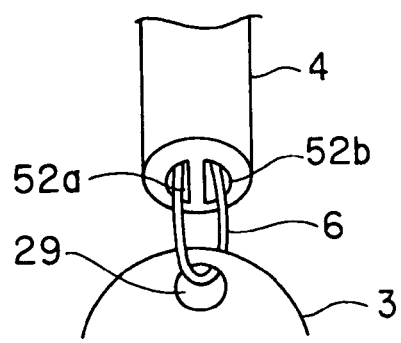
FIG. 5E is a diagram showing the structure in which a folded string member is inserted in two lumens.

The above description is given of the hollow portion of the tube member 4 comprising one lumen. Referring to FIG. 5E, two lumens 52a and 52b are formed, the string member 6 is bent in the lumens 52a and 52b, and the bent string member 6 may be inserted.

Further, the hardness and launching property of the tube member 4 may be partly changed. For example, the tube member 4 has the hardness and launching property that it is not easily bent except from the distal-end opening of 10 cm only the distal end of 10 cm on the opening is softer than other portion. Thus, the operability of the capsule 3 and the easy swallowing of the patient are established. The hardness or launching property may be changed stepwise or may be changed continuously and gradually.

Preferably, the string member 6 has the preferable smoothness and high strength although the diameter is thin. For example, the string member 6 can use Teflon®, nylon string, a string for operation, or gut.

When the capsule 3 reaches a stomach 57, the length of the tube member 4 may be set to 60 cm or more so that the rear end of the tube member 4 exists outside a mouth 53. The string member 6 may be set to twice or more of the length of the tube member 4.

Next, a description is given of the operation for examining the gastrointestinal tract by using the gastrointestinal tract examining apparatus 5 having the above structure with reference to FIGS. 6A to 6C.

Referring to FIG. 6A, the syringe 39 including the iodine solution 43 is attached to the tube member hand portion 36 of the gastrointestinal tract examining apparatus 5. The rear end of the tube member hand portion 36 in which the string member 6 is covered by the stopper member 41, thereby preventing the unnecessary movement of the string member 6.

The patient 2 swallows the capsule 3 from a mouth 53. The capsule 3 swallowed from the mouth 53 is moved to an esophagus 55 via a throat 54. The esophagus 55 is divided into a top portion 55a on the throat 54 side, a middle 55b, and a bottom portion 55c near a cardia 56.

In the case of the single capsule 3, the capsule 3 passing through the throat 55 by the peristaltic movement of the esophagus 55 or the weight of the capsule 3, and reaches the stomach 57. According to the first embodiment, the capsule 3 is connected to the tube member 4 and therefore the moving speed of the capsule 3 at the distal end of the tube member 4 is set to be a desired speed by gripping the rear end side of the tube member 4 and pushing and pulling it. Further, the capsule 3 is stopped at an arbitrary position in the halfway of the esophagus 55, thereby examining in detail the body cavity.

The moving speed of the capsule 3 is set to the desired one and therefore the necessary number of images can be picked-up if the image pick-up speed of the capsule 3 is a relatively slow one, e.g., two images per second or less.

At the top portion 55a of the esophagus 55, if the inner wall thereof is checked in detail, referring to FIG. 6A, the syringe 39 containing the iodine solution 43 is operated while the capsule 3 is in the top portion 55a, and the iodine solution 43 is injected in the body near the top portion 55a via the hollow portion of the tube member 4. The injected iodine solution 43 is sprayed around the capsule 3, and is further sprayed to the inner wall surface of the top portion 55a.

As a result of spraying the dye of the iodine solution 43, the image picked-up by the capsule 3 is stained and the structure is further clear, thus to easily perform the diagnosis. That is, the examination using the iodine staining method is easy.

The capsule 3 completes the image pick-up operation of the portion to which the dye is sprayed and then the capsule 3 moves forward (to the deep portion), the dye may be further sprayed and the image may be picked-up.

The dye is not sprayed, then, the capsule 3 is moved to the bottom portion 55c from the top portion 55a of the esophagus 55, and the image is picked-up. After that, the tube member 4 is pulled out, it is pulled up (returned), the dye is sprayed in this state, and then the capsule 3 may pick-up the image.

That is, under different conditions including the examination without the dye staining and the examination with the dye staining, the examination is easily repeated. Since the pull-out operation is possible, the tube member 4 is pushed or pulled out, thereby changing the moving speed and repeating the examination.

According to the first embodiment, the capsule 3 is connected to the tube member 4. The proximal end of the extracorporeally-arranged tube member 4 is operated, thereby setting the capsule 3 to an arbitrary position. Further, the image pick-up operation can be performed again.

As mentioned above, the image pick-up operation and examination of the esophagus 55 end and, then, the capsule 3 passes through the cardia 56 and reaches the stomach 57.

The stomach 57 may be examined by the capsule 3 with a method shown in FIG. 6B. Referring to FIG. 6B, the two string members 6 extended from the tube member hand portion 36 are pushed and are pulled-out (are loosened and are towed) and the tube member 4 is rotated.

By pushing and pulling (loosening and towing) the string members 6, the two string members 6 which are projected from the distal end of the tube member 4 and are folded through the through-holes 29 are pushed and are pulled out (are loosened and towed). Further, the capsule 3 is rotated as shown by an arrow A from a state shown by a solid line in FIG. 6B to a state shown by a two-dotted line, thereby changing the direction of field of view so as to examine the stomach 57 within the wide range thereof.

By twisting and rotating the tube member 4, the distal end of the tube member 4 is rotated as shown by an arrow B in FIG. 6B. In this state, the stomach 57 is examined within the wide range by changing the field of view.

After examining the stomach 57, only one of the two string members 6 is pulled out. Another string member 6 is moved to the distal end side of the tube member 4. Thus, referring to FIG. 6C, the locking state due to the folding operation is reset, then, the capsule 3 is detached from the string member 6, the capsule 3 falls in the stomach 57, and the capsule 3 is detached from the tube member 4.

The capsule 3 fallen in the stomach 57 moves to a duodenum 58 side by the peristaltic movement of the stomach 57. The capsule 3 picks-up the image at a constant period. The picked-up image data is transmitted by radio waves, and the transmitted image data is stored in the storing means 33 of the extracorporeal unit 8. Further, the image picked-up by the liquid crystal monitor 18 can be confirmed.

The image pick-up speed of the capsule 3 after detachment may be the same, or may be increased from two images per second before the detachment to four images per second or more after the detachment. When the moving speed of the capsule 3 after the detachment is increased, the necessary number of images is picked-up by increasing the image pick-up speed. The image pick-up speed upon detachment is changed by transmitting a signal for changeling the image pick-up speed to the capsule 3 arranged in the body from the extracorporeal unit 8. Or, a timer is included in the capsule 3, and the image pick-up speed may be automatically switched by the time after starting the examination (e.g., 10 minutes).

Figure 7:
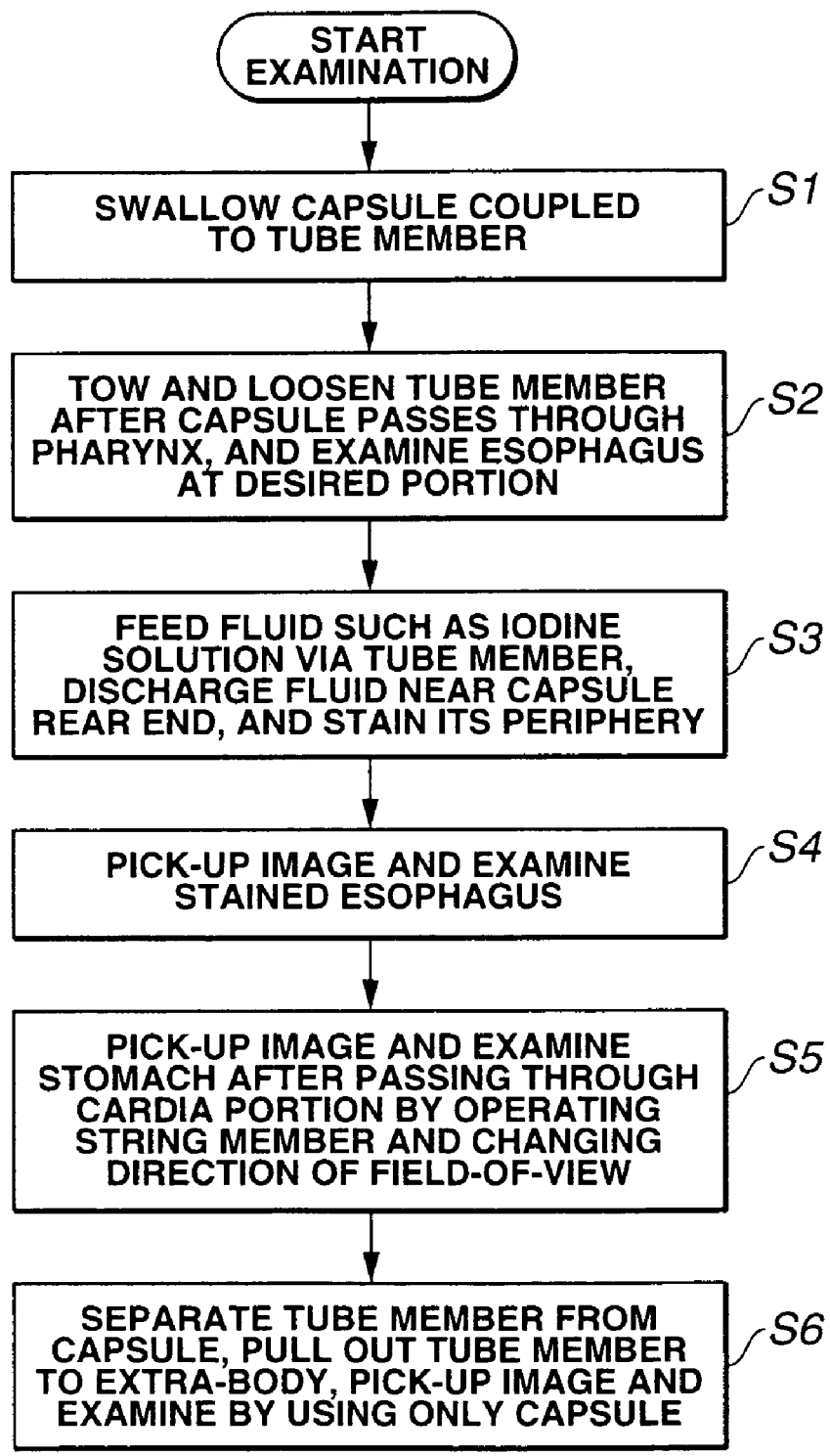

FIG. 7 shows a typical example of the above-mentioned examining method. In step S1, the capsule 3 is connected to the tube member 4 and then the capsule 3 is swallowed. In step S2, the capsule 3 passes through the pharynx and then the capsule 3 performs the endoscope examination (image pick-up operation and examination) of the esophagus 55 at the desired position while towing and loosening the tube member 4.

In step S3, the fluid for staining such as the iodine solution 43 is transmitted to the tube member 4 from the outside of the body, the fluid is discharged near the rear end of the capsule 3 (injected to the esophagus 55 side) from the distal end of the tube member 4, and the periphery is stained.

In step S4 after discharging the fluid, the image of the stained esophagus 55 is picked-up and is examined.

In step S5, the capsule 3 reaches the stomach 57 after passing through the cardia 56, and then the direction of the field of view of the capsule 3 is changed by operating a plurality of string members 6. Further, the image pick-up operation and examination are performed.

In step S6, the tube member 4 is detached from the capsule 3, only the tube member 4 is pulled out to the outside of the body, and the image pick-up operation and the examination are performed by only the capsule 3.

Thus, the portion from the esophagus 55 to the stomach 57 is examined in detail with the endoscope. The tube member 4 is detached from the capsule 3 after the examination and the stomach 7 is examined with the endoscope by only the capsule 3.

According to the first embodiment, it is possible to perform both the returning observation of the esophagus 55 and the untethered observation of the deep portion from the stomach 57 with the easy method.

Further, the stomach 57 is observed within the wide range from the cardia 56 with the easy method. Further, advantageously, the esophagus 55 is observed with the dye at the desired position with the easy method.

Second Embodiment

Figure 8A:
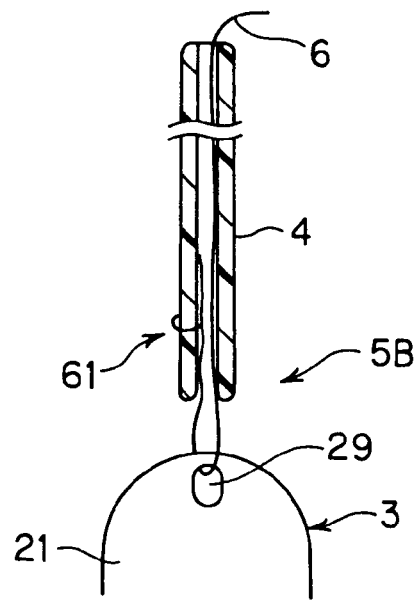
FIGS. 8A and 8B relate to a second embodiment of the present invention.
Figure 8B:
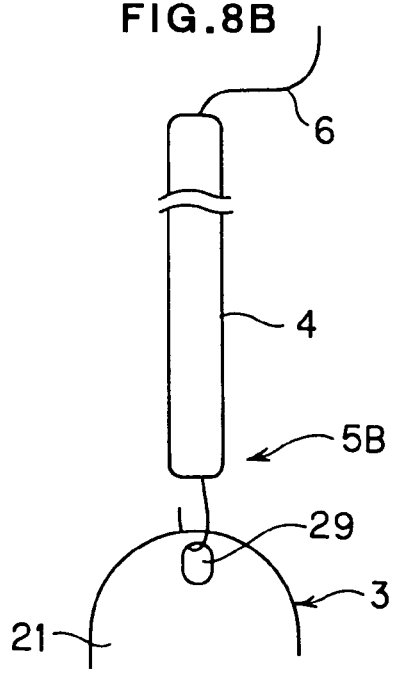

Next, a description is given of a gastrointestinal tract examining apparatus according to a second embodiment of the present invention with reference to FIGS. 8A and 8B. According to the first embodiment, the two folded string members 6 are inserted in the hollow portion of the tube member 4. However, referring to FIG. 8A, in a gastrointestinal tract examining apparatus 5B according to the second embodiment, the folded string members 6 through the through-hole 29 of the capsule 3 are inserted in the halfway of the hollow portion of the tube member 4. For example, near the distal end of the tube member 4, a temporary stop portion 61 is formed to temporarily stop the tube member 4 by sewing the tube member 4 through the side surface or adhering the tube member 4 to the side surface with an adhesive.

The inserting tool 45 such as a wire or a needle member may be attached to the distal end of the string member 6 as shown in FIG. 4A and further may be inserted in the tube member 4 near the distal end of the tube member 4. Alternatively, the temporary portion 61 for temporary stop may be formed by previously arranging many through-holes near the distal end of the tube member 4 and by passing through the tube member 4 through the through-holes for easy insertion.

In this case, the string members 6 are adhered like a loop with an adhesive and are locked, therefore, the string members 6 extended from the rear end of the tube member 4 are strongly pulled-out, and the temporary stop state of the temporary stop portion 61 is solved as shown in FIG. 8B. Further, the string member 6 is pulled out to the rear side, thereby setting the tube member 4 side apart from the capsule 3.

According to the second embodiment, the tube member hand portion 36 shown in FIG. 3 is not arranged to the rear end of the tube member 4. In the case of the observation by spraying the dye according to the first embodiment, the tube member hand portion 36 may be arranged. Further, by the pressing and the insertion, the tube member hand portion 36 may be detachably attached to the rear end of the tube member 4. According to the second embodiment, other structures are the same as those according to the first embodiment.

The examining method according to the second embodiment is similar to that according to the first embodiment. Briefly, in the case of examining the esophagus 55 as shown in FIG. 6A, the tube member 4 is connected to the capsule 3, that is, the esophagus 55 is examined in a state shown in FIG. 8A.

The esophagus 55 is examined, the capsule 3 reaches the stomach 57 and, then, the string member 6 extended from the rear end of the tube member 4 is strongly pulled out, thereby detaching the string member 6 which is temporarily stopped on the distal end side thereof. Thus, the tube member 4 is detached from the capsule 3.

After that, by pulling out the tube member 4, the tube member 4 is pulled out to the outside of the body, and the tube member 4 is disposed. The capsule 3 falls in the stomach 57, it moves to the duodenum 58 side by the peristaltic movement, further, it moves to the small intestine and the large intestine by the peristaltic movement, and the capsule 3 picks-up the image in this case. That is, the endoscope examination is performed. The image data picked-up by the capsule 3 is transmitted to the extracorporeal unit 8 by radio waves. The transmitted image data is stored in the storing means 33 in the extracorporeal unit 8. The liquid crystal monitor 18 checks the picked-up image.

According to the second embodiment, the tube member 4 is certainly detached from the capsule 3 with the low operating amount for the pulling-out operation. In addition, the same advantages as those according to the first embodiment are obtained.

Third Embodiment

Figure 9A:
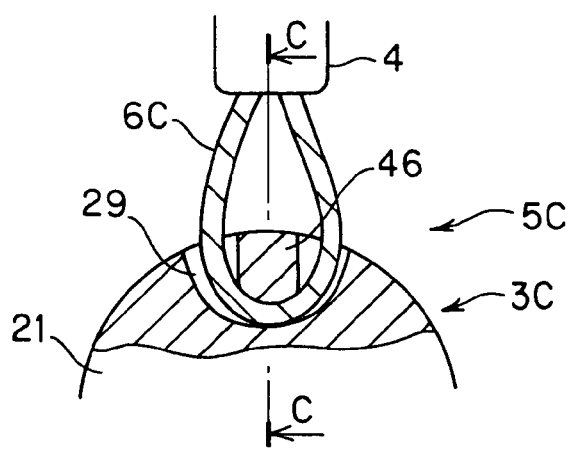
FIGS. 9A to 9D relate to a third embodiment of the present invention.
Figure 9B:
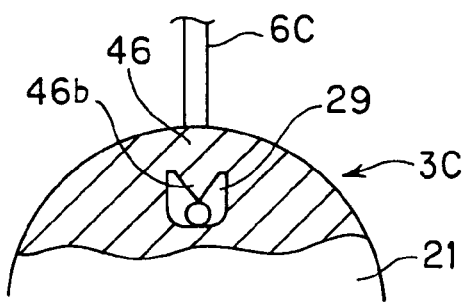

Next, a description is given of a gastrointestinal tract examining apparatus according to a third embodiment of the present invention with reference to FIGS. 9A to 9D. Referring to FIGS. 9A and 9B, a gastrointestinal tract examining apparatus according to third embodiment has a structure near the through-hole 29 in a capsule 3C as a feature. According to the third embodiment, the string member 6 has a cotton thread 6C which is easily cut. In addition to the cotton thread 6C, a thread which is soft and is easily cut may be used, such as wool.

In the capsule 3C according to third embodiment, a locking portion 46 shown in FIG. 4C in the capsule 3 according to the first embodiment has a projected portion 46b as a sharp portion which is notch-shaped, at the portion through which a cotton thread 6C passes like the U-shape.

That is, a sharp projected portion 46b as shown in FIG. 9B is formed on a C-C cross section in FIG. 9A.

Figure 9C:
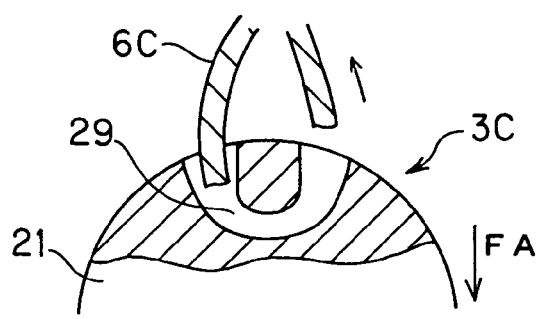

In the state in FIG. 9A, by strongly pulling the cotton thread 6C, the projected portion 46b cuts the cotton thread 6C as shown in FIG. 9C. Thus, the cotton thread 6C on the tube member 4 is detached from the capsule 3C. The detached capsule 3 falls down. Other structures are the same as those according to the first embodiment or the second embodiment.

Advantages according to the third embodiment are the same as those according to the second embodiment. That is, the user strongly pulls the cotton thread 6C, thereby easily detaching the tube member 4 from the capsule 3C.

Figure 9D:
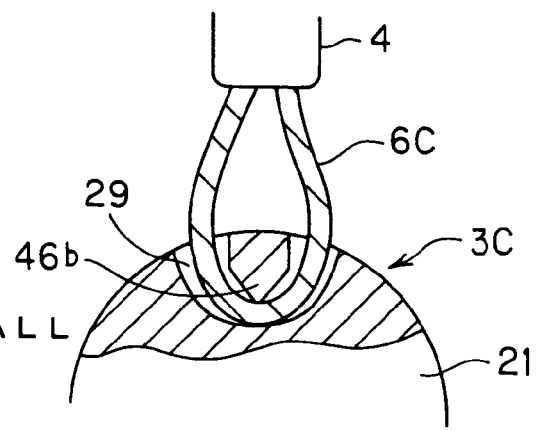

According to the third embodiment, the C-C cross section shown in FIG. 9A is shown in FIG. 9B. However, the cross section in FIG. 9A has the structure in which the sharp projected portion 46b is formed to the locking portion 46 as shown in FIG. 9D so as to prevent the appearance of the sharp projected portion 46b on the C-C cross section in this case.

Fourth Embodiment

Figure 10A:
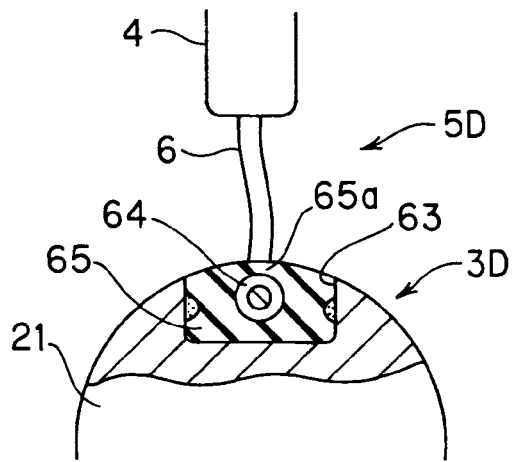
FIGS. 10A and 10B relate to a fourth embodiment of the present invention.
Figure 10B:
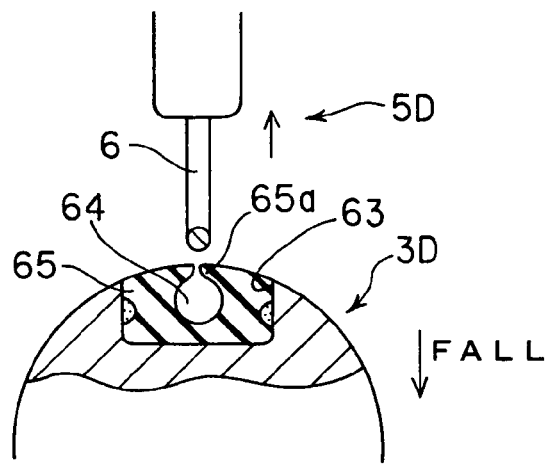

Next, a description is given of a gastrointestinal tract examining apparatus according to a fourth embodiment of the present invention with reference to FIGS. 10A and 10B. A gastrointestinal tract examining apparatus 5D according to the fourth embodiment comprises: the tube member 4 in which the string member 6 is inserted; and a capsule 3D to which the tube member 4 is connected via the string member 6.

In place of the through-hole 29, the capsule 3D has a caved portion 63 at the rear end of the exterior member main body 21 according to the first embodiment, and the caved portion 63 accommodates therein an elastic member 65 having a through-hole 64 which is fixed by an adhesive 66 (or by pressing).

The elastic member 65 contains urethan or silicone rubber, the through-hole 64 thereof is arranged to a portion near the outer surface, and the thickness of the arranged portion of the through-hole 64 has a thin portion 65a. Strong force is applied to the thin portion 65a and thus the thin portion 65a is set to be broken. Other structures are the same as those according to the second embodiment.

The examining method according to the fourth embodiment is similar to that according to the second embodiment. According to the fourth embodiment, the operation is different upon detaching the tube member 4 from the capsule 3D, and therefore the operation in this case will be described.

According to the fourth embodiment, referring to FIG. 10A, the string member 6 is pierced through the through-hole 64 of the elastic member 65 and, simultaneously, the two string members 6 inserted in the tube member 4 are strongly towed. Consequently, referring to FIG. 10B, the thin portion 65a of the elastic member 65 is broken. This break separates the tube member 4 from the capsule 3D, and the capsule falls down.

The advantages according to the fourth embodiment are the same as those according to the second embodiment.

Figure 11A:
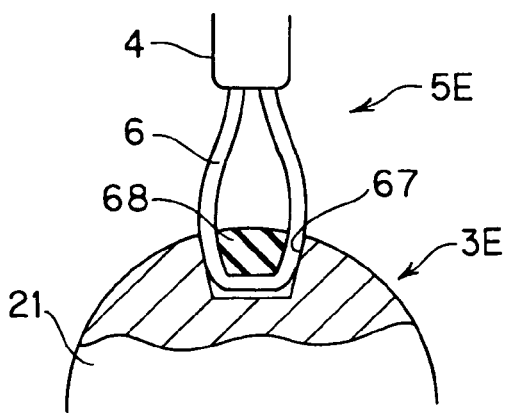
FIGS. 11A and 11B are diagrams showing the structure of a main portion of a gastrointestinal tract examining apparatus according to a first modification of the fourth embodiment of the present invention.

FIG. 11A shows a gastrointestinal tract examining apparatus 5E according to a first modification of the fourth embodiment of the present invention. A capsule 3E according to the first modification has a caved portion 67, similarly to the capsule 3D shown in FIG. 10A. The caved portion 67 is taper-shaped with a wide portion on the opening end side.

The string member 6 which is folded like U is inserted into the caved portion 67. After inserting the string member 6, an elastic member such as a rubber stopper 68 is pressed in from the top of the folded portion of the string member 6, and thus the tube member 4 is connected to the capsule 3E.

Figure 11B:
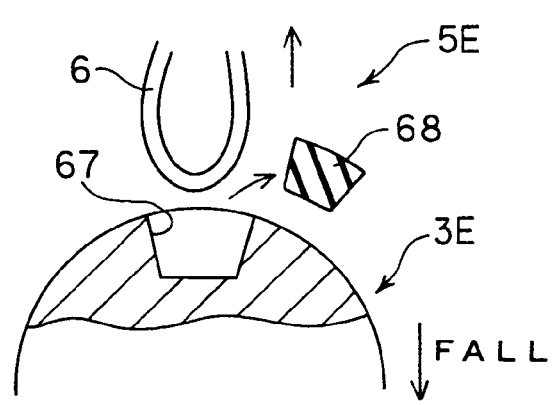

According to the first modification of the fourth embodiment, the string member 6 is strongly towed to the rear side, thereby detaching, from the caved portion 67, the rubber stopper 68 pressed in the caved portion 67 as shown in FIG. 11B. In addition, the same operations and advantages as those according to third embodiment are obtained according to the first modification.

Further, according to the first modification, the rubber stopper 68 is pressed in from the top of the string member 6 accommodated in the caved portion 67. In this state, the caved portion 67 and the rubber stopper 68 form a through-hole as shown in FIG. 11A.

Figure 12A:
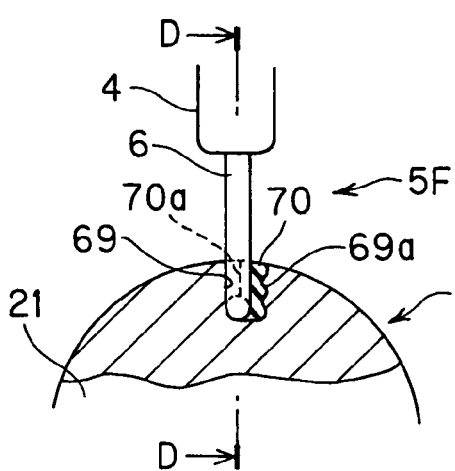
FIGS. 12A and 12B are diagrams showing the structure of a main portion of a gastrointestinal tract examining apparatus according to a second modification of the fourth embodiment of the present invention.
Figure 12B:
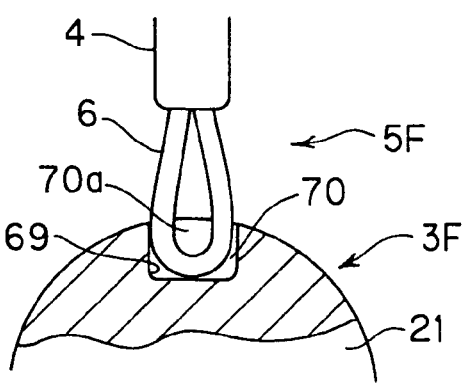

On the contrary, referring to FIGS. 12A and 12B, in a gastrointestinal tract examining apparatus 5F according to the second modification of the fourth embodiment, even when a rubber stopper 70 is pressed in the caved portion 69 of a capsule 3F but any through-holes are not formed, the tube member 4 can be connected to the capsule 3F.

According to the second modification, referring to FIG. 12A, the capsule 3F has the caved portion 69 like the capsule 3E. The caved portion 69 has one inner surface as a plane surface, and another inner surface facing the plane surface has a caved and projected portion 69a. FIG. 12B shows a D-D cross-section in FIG. 12A.

By pressing, in the caved portion 69, the rubber stopper 70 and the string member 6 which is inserted in the tube member 4 and is folded like loop, the tube member 4 is connected to the capsule 3F.

In this case, the rubber stopper 70 is compressed at the bottom portion of the caved portion 69. The top portion of the rubber stopper 70 has a projected portion 70a which is projected to the folded string member 6 side.

Thus, by towing the string member 6 to the rear side, the rubber stopper 70 and the string member 6 are moved to the top side from the bottom surface of the caved portion 69.

In this case, the caved portion 69 has the caved and projected portion 69a in the depth direction of the caved portion 69 and therefore the pitch movement of the caved and projected portion 69a is felt like the click operation upon towing the string member 6. In the cases shown in FIGS. 12A and 12B, after the click operation is performed twice, the string member 6 is further towed, thereby the tube member 4 from the capsule 3F. Other advantages are the same as those according to third embodiment.

Fifth Embodiment

Figure 13A:
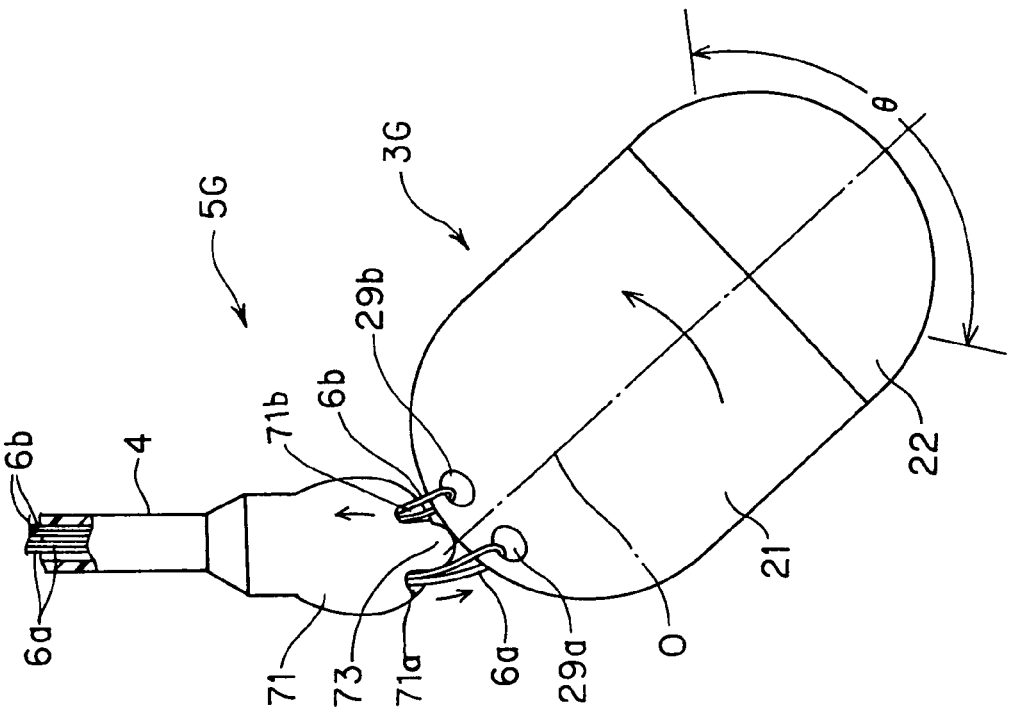
Figure 13B:
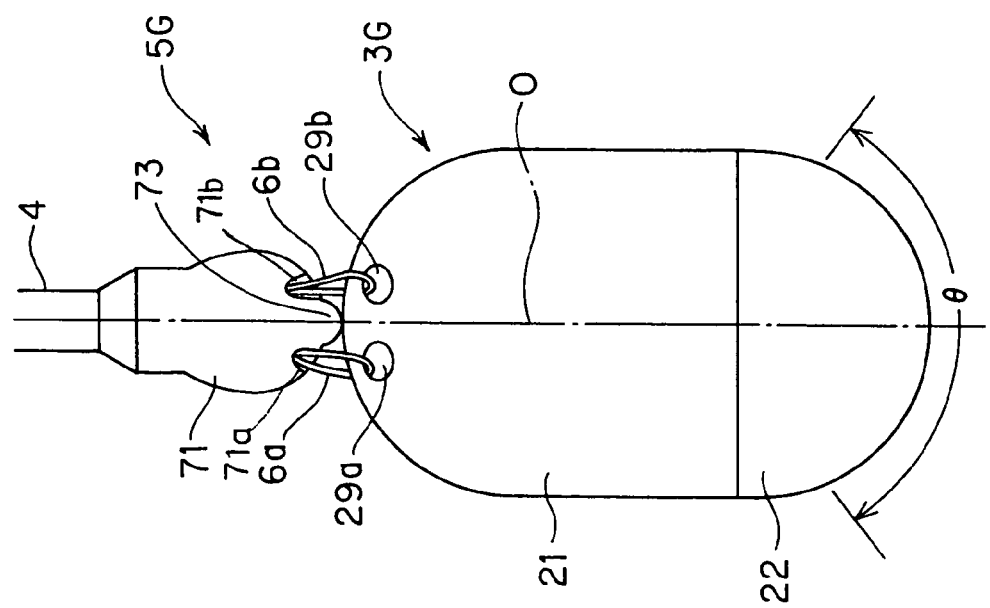
FIG. 13B is a diagram showing a state in which tractive force generated by first and second string members is relatively changed in FIG. 13A.
Figure 14:
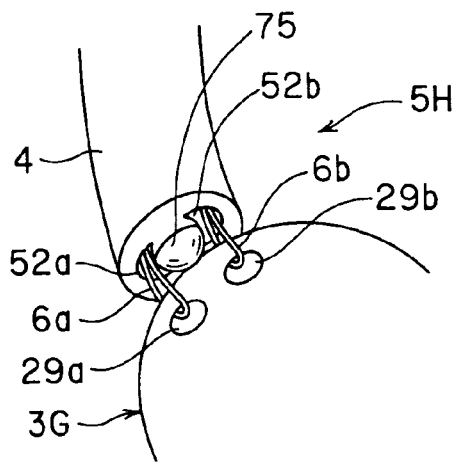

Next, a description is given of a gastrointestinal tract examining apparatus according to a fifth embodiment of the present invention with reference to FIGS. 13A to 14.

A gastrointestinal tract examining apparatus 5G according to the fifth embodiment comprises a capsule 3G having two through-holes 29a and 29b, the tube member 4 having a distal end member 71 at the distal end thereof, and first and second string members 6a and 6b which are inserted in the hollow portion of the tube member 4.

In the capsule 3G, in place of the one through-hole 29 at the rear end of the exterior member main body 21, the two first and second through-holes 29a and 29b are symmetrically formed on both sides of an observing central axis O. The observing central axis O matches the optical axis of the optical system 23 in the capsule 3G. Reference symbol θ denotes an observing range of the optical system 23.

The distal end member 71 attached to the distal end of the tube member 4 is shaped to be symmetrical for rotation with the outer diameter larger than that of the tube member 4. The distal end portion of the distal end member 71 has a projected portion 73 which is spherical.

Near the base of the spherical projected portion 73 of the distal end member 71, two openings 71a and 71b are arranged to the positions facing the first and second through-holes 29a and 29b to be inserted in the hollow portion of the tube member 4.

The first and second string members 6a and 6b are inserted in the hollow portion of the tube member 4 and are projected from the openings 71a and 17b arranged to the distal end member 71, are folded via the first and second through-holes 29a and 29b of the facing capsule 3G, and are inserted in the hollow portion of the tube member 4 via the openings 71a and 71b again. Thus, the tube member 4 is connected to the capsule 3G.

According to the fifth embodiment, when setting, to be equal, the tractive force affected to the capsule 3G which is caused by the first and second string members 6a and 6b, referring to FIG. 13A, the distal end portion of the semi-spherical projected portion 73 of the distal end member 71 is in contact with the rear end of the exterior member main body 21 on the observing central axis O and thus the tube member 4 is connected to the capsule 3G.

On the contrary, by relatively changing the tractive force affected to the capsule 3G which is caused by the first and second string members 6a and 6b, referring to FIG. 13B, the direction of the observing central axis O of the capsule 3G is inclined from the longitudinal direction of the tube member 4.

The user loosens the first string member 6a and tows the second string member 6 as shown in FIG. 13B, thereby bending or inclining the capsule 3G to the second string member 6b. As mentioned above, one of the first string member 6a and the second string member 6b is towed and another is loosened. Thus, the capsule 3G is inclined and the direction of the observing central axis O is varied and is set.

The image pick-up operation and the examination are possible within the wide range. Therefore, as mentioned with reference to FIG. 6B the inner wall surface of the stomach 57 is examined within the wide range. Further, by the operation shown in FIG. 13B, the esophagus 55 is examined in detail by changing the observing direction. Other advantages are the same as those according to the first and second embodiments.

According to a modification of the fifth embodiment with reference to FIG. 14, a gastrointestinal tract. examining apparatus 5H may be used. According to the modification of the fifth embodiment, the tube member 4 is formed by double lumen tubes having two lumens 52a and 52b shown in FIG. 5E. Further, the first and second string members 6a and 6b are projected from the lumens 52a and 52b, and the tube member 4 is connected to the capsule 3G via the first and second through-holes 29a and 29b.

A semi-spherical projected portion 75 is arranged in the center of the distal end surface of the tube member 4.

The projected portion 75 is abutted against the surface at the rear end of the capsule 3G, and one of the first and second string members 6a and 6b is towed and another is loosened, thereby changing the observing direction of the capsule 3G.

According to the modification, the same operations and advantages according to the fifth embodiment are obtained.

Further, according to another modification, four lumens may be arranged, in place of the tow lumens 52a and 52b.

Sixth Embodiment

Figure 15:
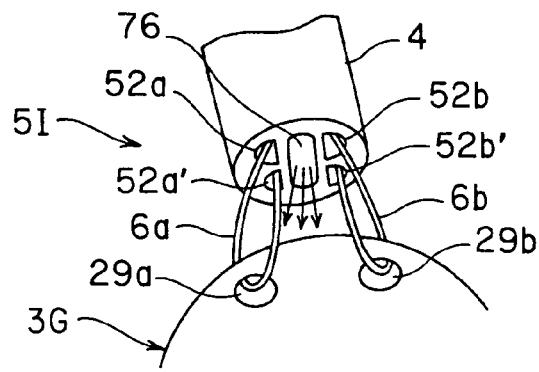
FIG. 15 is a diagram showing the structure of a main portion of a gastrointestinal tract examining apparatus according to a sixth embodiment of the present invention.

Next, a description is given of a gastrointestinal tract examining apparatus according to a sixth embodiment of the present invention with reference to FIG. 15. In a gastrointestinal tract examining apparatus 5I according to the sixth embodiment, four lumens 52a, 52a', 52b, and 52b' are arranged, in place of the tow lumens 52a and 52b shown in FIG. 14. Further, the tube member 4 has a lumen 76 for injecting the liquid, place of the projected portion 75.

A portion similar to the tube member hand portion 36 according to the first embodiment is connected to the rear end side of the tube member 4, thereby injecting a therapeutic drug solution or iodine solution via the lumen 76 for injecting the liquid.

According to the sixth embodiment, the same advantages as those according to the first embodiment are obtained.

Seventh Embodiment

Figure 16:
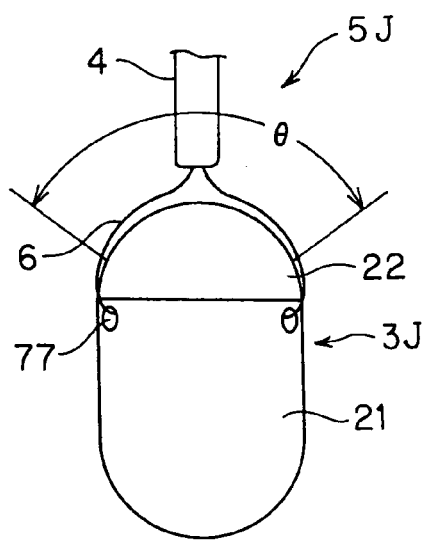
FIG. 16 is a diagram showing the structure of a main portion of a gastrointestinal tract examining apparatus according to a seventh embodiment of the present invention.

Next, a description is given of a gastrointestinal tract examining apparatus according to a seventh embodiment of the present invention with reference to FIG. 16. A gastrointestinal tract examining apparatus 5J according to the seventh embodiment comprises: a capsule 3J having a through-hole 77 near the bas end of the transparent cover 22; and the tube member 4 in which the string member 6 is inserted. The through-hole 77 is formed to be pierced through a portion with the similar diameter of the capsule 3J.

The string member 6 pierces through the through-hole 77 arranged to the capsule 3J from the distal-end opening of the tube member 4, thereby connecting the tube member 4 to the capsule 3J via the string member 6.

In this case, the through-hole 77 is formed near the distal end side having the transparent cover 22, rather than in center of the capsule 3J in the longitudinal direction. Therefore, when the tube member 4 is connected to the capsule 3J via the string member 6, the transparent cover 22 faces the tube member 4. The through-hole 77 is formed out of the observing field of view θ.

According to the seventh embodiment, the observing direction (image pick-up direction is opposite to that according to the first embodiment. Except for the different observing direction, the same advantages as those according to the first and second embodiments are obtained.

Eighth Embodiment

Figure 17A:
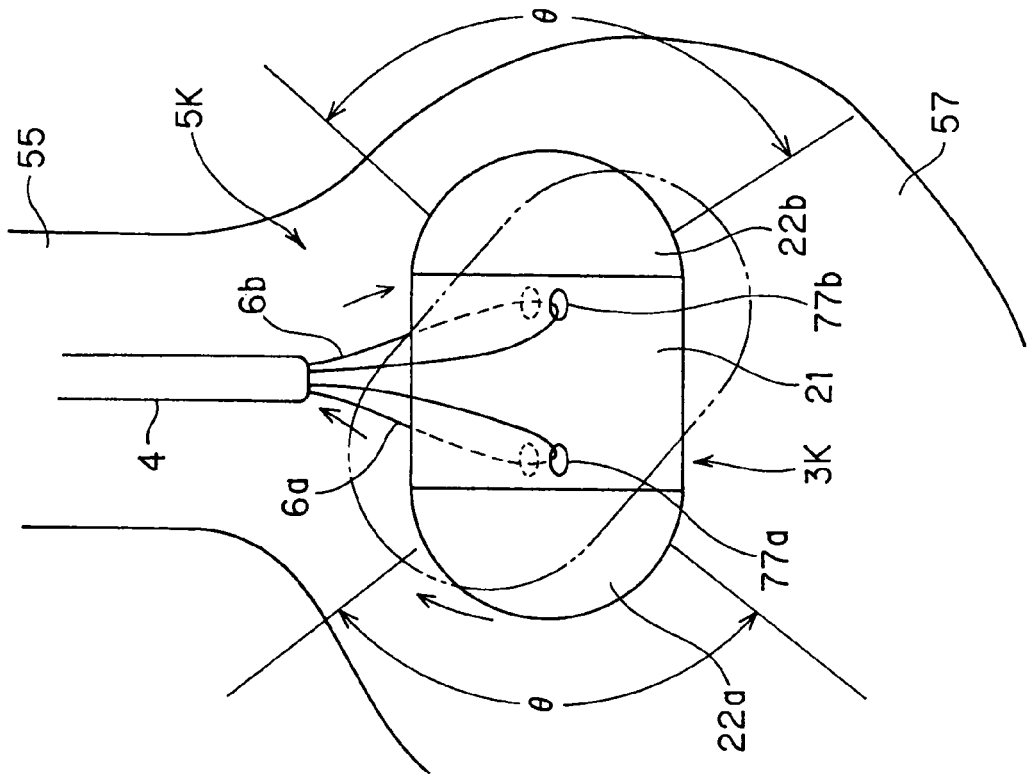
FIGS. 17A and 17B relate to an eighth embodiment of the present invention.
Figure 17B:
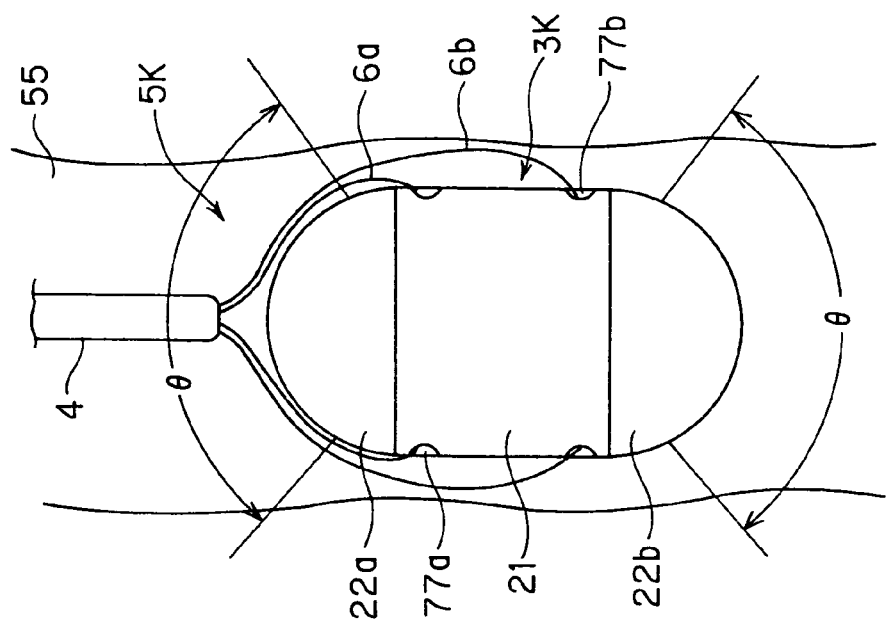

Next, a description is given of a gastrointestinal tract examining apparatus according to an eighth embodiment of the present invention with reference to FIGS. 17A and 17B. A gastrointestinal tract examining apparatus 5K according to the eighth embodiment comprises: a capsule 3K having transparent covers 22a and 22b at both ends; and the tube member 4 in which the first and second string members 6a and 6b are inserted.

The optical system 23, the image pick-up element 24, and the illuminating portion 25 are arranged to the inside of the transparent covers 22a and 22b. Reference symbol θ denotes the observing ranges of the optical systems.

Through-holes 77a and 77b are provided for the exterior member main body 21 near the base end of the transparent covers 22a and 22b, and the first and second string members 6a and 6b are inserted into the through-holes 77a and 77b.

Hereinbelow, a description is given of an examining method according to the eighth embodiment with reference to FIGS. 17A and 17B. Referring to FIG. 17A, when examining the luminal portion with the outer diameter of the capsule 3K like the esophagus 55, the first and second string members 6a and 6b are operated so that the longitudinal direction of the capsule 3K is along the longitudinal direction of the luminal portion.

For example, by strongly towing the first string member 6a rather than the second string member 6b, the state shown in FIG. 17A is set, thereby examining the esophagus 55.

On the contrary, when examining the stomach 57 which is much larger than the size of the capsule 3K, the tractive force of the first string member 6a is equal to that of the second string member 6b, thereby setting the state long in the horizontal direction as shown in FIG. 17B.

After the observation in this state, by strongly towing the first string member 6a rather than the second string member 6b, the capsule 3K is inclined as shown by a two-dotted line. As mentioned above, by towing the first string member 6a and the second string member 6b, the stomach 57 is examined by widely changing the observing direction in the stomach 57.

Other advantages are the same as those according to the first embodiment.

Another embodiment obtained by partly combining the first to eight embodiments belong to the present invention. Although the image pick-up operation and the examination (endoscope examination) are optical, the present invention can be applied to the therapeutic medical treatment by spraying the drug solution and the examination except for the optical one, such as pH sensing or ultrasonic examination.

Having described the preferred embodiments of the invention referring to the accompanying drawings. It should be understood that the present invention is not limited to those precise embodiments and various changes and modifications thereof could be made by one skilled in the art without departing from the spirit of scope of the invention as defined in the appended claims.

What is claimed is:

1. A gastrointestinal tract examining apparatus comprising:
   a capsular endoscope which examines the gastrointestinal tract;
   a flexible tube;
   a connecting portion arranged on the capsular endoscope, and a flexible string which is inserted in the flexible tube and releasably engages the connecting portion to connect the flexible tube to the capsular endoscope;

wherein the flexible tube is separated from the capsular endoscope by detaching the flexible string from the connecting portion, and wherein the connecting portion is a through-hole which is arranged to the capsular endoscope, and the capsular endoscope is detachably connected to the tube by inserting the flexible string in the through-hole, and wherein the peripheral portion of the through-hole has a sharp portion which cuts the flexible string by towing the flexible string with a force of a certain level or more, or has a thin portion which will break, or which will fall down from the peripheral portion of the through-hole by towing the flexible string with force of a certain level or more.

2. The gastrointestinal tract examining apparatus according to claim 1, wherein the outer diameter of the flexible tube has a diameter which is at most half of the outer diameter of the capsular endoscope.

3. The gastrointestinal tract examining apparatus according to claim 2, wherein the outer diameter of the flexible tube is 5 mm or less.

4. The gastrointestinal tract examining apparatus according to claim 2, wherein the flexible tube has flexibility that it is not easily bent by tractive force of the flexible string inserted in the flexible tube.

5. The gastrointestinal tract examining apparatus according to claim 1, further comprising:

holding means which detachably holds the end portion of the flexible string near the proximal end of the flexible tube.

6. The gastrointestinal tract examining apparatus according to claim 1, wherein one tip of the flexible string is detachably fixed by a fixing portion arranged in the flexible tube, and another end of the flexible string is inserted from the distal end of the flexible tube to the proximal end via the connecting portion arranged to the capsular endoscope.

7. The gastrointestinal tract examining apparatus according to claim 6, wherein one tip of the flexible string is detachably fixed by the fixing portion arranged near the distal end of the flexible tube.

8. The gastrointestinal tract examining apparatus according to claim 1, wherein the outer surface of the distal end portion of the flexible tube has an R-shaped chamfering portion to the outer surface of the distal end portion of the flexible tube.

9. The gastrointestinal tract examining apparatus according to claim 1, wherein the flexible tube has, at the distal end portion thereof, a semi-spherical distal end member independent of the flexible tube.

10. The gastrointestinal tract examining apparatus according to claim 1, wherein a distal end of the flexible tube is softer than a proximal end of the flexible tube.

11. The gastrointestinal tract examining apparatus according to claim 10, wherein a predetermined length of the distal end of the flexible tube is softer Than other portions of the flexible tube.

12. The gastrointestinal tract examining apparatus according to claim 10, wherein the flexible tube has a hardness which varies along its length.

13. The gastrointestinal tract examining apparatus according to claim 1, wherein the flexible tube has a fluid injecting portion at a vicinity of a proximal end of the flexible tube for injecting one or more of liquid and air into the flexible tube.

14. The gastrointestinal tract examining apparatus according to claim 1, wherein a plurality of the through-holes are arranged at a predetermined spacing, each of a plurality of flexible strings inserted into the plurality of through-holes are inserted in the flexible tube, and at least one tip of the plurality of flexible strings extends from the proximal end of the flexible tube.

15. The gastrointestinal tract examining apparatus according to claim 14, wherein the plurality of flexible strings are individually tensioned or loosened, thereby oscillating the capsular endoscope.

16. The gastrointestinal tract examining apparatus according to claim 14, wherein the flexible tube is a multi-lumen tube having a number of lumens corresponding to at least a number of flexible strings.

17. The gastrointestinal tract examining apparatus according to claim 1, wherein the flexible tube is a multi-lumen tube having a number of lumens corresponding to at least twice a number of flexible strings.

18. The gastrointestinal tract examining apparatus according to claim 1, wherein the flexible tube is a torque tube formed by one of embedding a metallic net into resin, embedding a metallic spiral member into resin, a tube containing fluorocarbon resin and a resin tube.

19. The gastrointestinal tract examining apparatus according to claim 1, wherein the flexible string comprises a thread formed from one of a fluorocarbon resin and nylon string.

20. The gastrointestinal tract examining apparatus according to claim 1, wherein the flexible string is a thread which is soft and is easily cut such as a cotton thread, silk thread, polyester yam, and wool thread.

21. An examining method comprising the steps of:

releasably connecting a capsular endoscope to a flexible tube by a flexible string arranged in the flexible tube, wherein the entirety from a distal end to a proximal end of the flexible string is formed by a single flexible member, and the flexible string engages a connecting portion of the capsular endoscope;

swallowing the connected capsular endo scope;

performing the endoscope examination of a desired portion by towing or loosening the flexible tube after the capsular endoscope passes through the throat; and separating the flexible tube from the capsular endoscope by pulling out the flexible string at a desired position.

22. The examining method according to claim 21, further comprising the step of:

performing the endoscope examination with the single capsular endoscope after the step of separating the tube member from the capsular endoscope.

23. An examining method comprising the steps of:

releasably connecting a capsular endoscope to a flexible tube by a flexible string arranged in the flexible tube, wherein the entirety from a distal end to a proximal end of the flexible string is formed by a single flexible member, and the flexible string engages a connecting portion of the capsular endoscope;

swallowing the connected capsular endoscope;

performing the endoscope examination of a desired portion by towing or loosening the flexible tube after the capsular endoscope passes through the throat;

transmitting a fluid to a tube from the outside of the body, and discharging the fluid near the rear end of the capsular endoscope from the distal end of the flexible tube;

performing the endoscope examination after discharging the fluid; and separating the flexible tube from the capsular endoscope by detaching the flexible string from the connecting portion at a desired position.

24. The examining method according to claim 23, wherein the fluid contains a dye.

25. An examining method comprising the steps of:
connecting a capsular endoscope to a flexible tube by a plurality of flexible strings arranged in the flexible tube, wherein the entirety from distal ends to proximal ends of the plurality of flexible strings are formed by a single flexible member;
swallowing the capsular endoscope connected to the flexible tube;
changing the direction of the field of view of the capsular endoscope by operating one or more of the plurality of flexible strings after the capsular endoscope passes through the cardia or throat and while the capsular endoscope is connected to the flexible tube;
separating the flexible tube from the capsular endoscope by pulling the flexible strings at a desired position; and
pulling only the flexible tube to the outside of the body.

26. A gastrointestinal tract examining apparatus comprising:
a capsular endoscope which examines the gastrointestinal tract;
a flexible tube member;
a flexible string member which is inserted in the tube member; and
a connecting portion which is arranged to the capsular endoscope,
wherein the tube member is separated from the capsular endoscope by detachably connecting the string member to the connecting portion, the connecting portion is a through-hole which is arranged to the capsular endoscope, and the capsular endoscope is detachably connected to the tube member by inserting the string member in the through-hole and the peripheral portion of the through-hole has a sharp portion which cuts the string member by tensioning the string member with a force of a predetermined magnitude.

27. A gastrointestinal tract examining apparatus comprising:
a capsular endoscope which examines the gastrointestinal tract;
a flexible tube member;
a flexible string member which is inserted in the tube member; and
a connecting portion which is arranged to the capsular endoscope,
wherein the tube member is separated from the capsular endoscope by detachably connecting the string member to the connecting portion, the connecting portion is a though-hole which is arranged to the capsular endoscope, and the capsular endoscope is detachably connected to the tube member by inserting the string member in the though-hole and the peripheral portion of the though-hole has a thin portion which will one of break and release from the peripheral portion of the though-hole by tensioning the string member with a force of a predetermined magnitude.

28. A gastrointestinal tract examining apparatus comprising:
a capsular endoscope which examines the gastrointestinal tact;
a flexible tube member;
a flexible string member which is inserted in the tube member; and
a connecting portion which is arranged to the capsular endoscope,
wherein the tube member is separated from the capsular endoscope by detachably connecting the string member to the connecting portion, the connecting portion comprises a caved portion which is arranged to the capsular endoscope and a fitting member which is fit into the caved portion, and the capsular endoscope is detachably connected to the tube member by locking the string member into the caved portion with the fitting member and wherein the fitting member fit into the caved portion releases from the caved portion by tensioning the string member with a force of a predetermined magnitude.

* * * * *